United States Patent
Homma et al.

(10) Patent No.: US 11,382,842 B2
(45) Date of Patent: Jul. 12, 2022

(54) COSMETIC

(71) Applicants: Oji Holdings Corporation, Tokyo (JP); NIKKO CHEMICALS CO., LTD., Tokyo (JP)

(72) Inventors: Ikue Homma, Tokyo (JP); Takayuki Shimaoka, Tokyo (JP); Keiko Murakoso, Tokyo (JP); Akihito Uka, Tokyo (JP)

(73) Assignees: OJI HOLDINGS CORPORATION, Tokyo (JP); NIKKO CHEMICALS CO., LTD., Tokyo (JP)

( * ) Notice: Subject to any disclaimer, the term of this patent is extended or adjusted under 35 U.S.C. 154(b) by 0 days.

(21) Appl. No.: 15/750,115

(22) PCT Filed: Aug. 4, 2016

(86) PCT No.: PCT/JP2016/072961
§ 371 (c)(1),
(2) Date: Jul. 2, 2018

(87) PCT Pub. No.: WO2017/022830
PCT Pub. Date: Feb. 9, 2017

(65) Prior Publication Data
US 2018/0296446 A1    Oct. 18, 2018

(30) Foreign Application Priority Data

Aug. 4, 2015 (JP) .............................. JP2015-154035
Sep. 1, 2015 (JP) .............................. JP2015-172380

(51) Int. Cl.
| | |
|---|---|
| A61K 8/02 | (2006.01) |
| A61Q 19/00 | (2006.01) |
| A61K 8/73 | (2006.01) |
| A61Q 17/04 | (2006.01) |
| C08B 15/00 | (2006.01) |
| C08L 101/14 | (2006.01) |
| A61Q 1/02 | (2006.01) |
| A61Q 5/12 | (2006.01) |
| C08L 1/02 | (2006.01) |
| C08L 33/26 | (2006.01) |

(52) U.S. Cl.
CPC .............. *A61K 8/027* (2013.01); *A61K 8/73* (2013.01); *A61K 8/731* (2013.01); *A61Q 1/02* (2013.01); *A61Q 5/12* (2013.01); *A61Q 17/04* (2013.01); *A61Q 19/00* (2013.01); *C08B 15/00* (2013.01); *C08L 1/02* (2013.01); *C08L 33/26* (2013.01); *C08L 101/14* (2013.01); *A61K 2800/10* (2013.01); *A61K 2800/412* (2013.01); *A61K 2800/48* (2013.01); *A61K 2800/542* (2013.01); *A61K 2800/5424* (2013.01)

(58) Field of Classification Search
CPC combination set(s) only.
See application file for complete search history.

(56) References Cited

U.S. PATENT DOCUMENTS

| | | |
|---|---|---|
| 2016/0074289 A1 | 3/2016 | Hayashi et al. |
| 2016/0333116 A1 | 11/2016 | Nakatani et al. |

FOREIGN PATENT DOCUMENTS

| | | |
|---|---|---|
| CN | 103561717 A | 2/2014 |
| CN | 104704169 A | 6/2015 |
| EP | 1839499 A1 | 10/2007 |
| JP | 11-500455 A | 1/1999 |
| JP | 2000-26229 A | 1/2000 |
| JP | 2002-5216507 A | 8/2000 |
| JP | 2000-327516 A | 11/2000 |
| JP | 2006-342140 A | 12/2006 |
| JP | 2007-82415 A | 4/2007 |
| JP | 2008-48602 A | 3/2008 |
| JP | 2008-050376 A | 3/2008 |
| JP | 2008-106178 A | 5/2008 |
| JP | 2009-62332 A | 3/2009 |
| JP | 2010-37199 A | 2/2010 |
| JP | 2010-37200 A | 2/2010 |
| JP | 2010-37348 A | 2/2010 |
| JP | 2011-56456 A | 3/2011 |
| JP | 2011-57567 A | 3/2011 |
| JP | 2011-57746 A | 3/2011 |
| JP | 2012-126788 A | 7/2012 |
| JP | 2012-193139 A | 10/2012 |
| JP | 2013-127141 A | 6/2013 |
| JP | 2014-125690 A | 7/2014 |
| JP | 2014-141637 A | 8/2014 |
| JP | 2014-141675 A | 8/2014 |
| JP | 2014-220340 A | 11/2014 |

(Continued)

OTHER PUBLICATIONS

International Preliminary Report on Patentability and Written Opinion of the International Searching Authority (Forms PCT/IB/326, PCT/IB/338, PCT/IB/373 and PCT/ISA/237) for Application No. PCT/JP2016/072961, dated Feb. 15, 2018, with an English translation.

International Search Report and English translation (Forms PCT/ISA/220 and PCT/ISA/210) for Application No. PCT/JP2016/072961, dated Oct. 4, 2016.

Canadian Office Action dated Dec. 14, 2018, issued in corresponding Canadian Patent Application No. 2,997,023.

Extended Euopean Search Report dated Dec. 21, 2018, issued in corresporsding European Patent Applicatin No. 16833109.8.

(Continued)

*Primary Examiner* — Hasan S Ahmed
(74) *Attorney, Agent, or Firm* — Birch, Stewart, Kolasch & Birch, LLP

(57) ABSTRACT

It is an object of the present invention to suppress agglutination of ultrafine cellulose fibers, while using the ultrafine cellulose fibers as a thickener in a cosmetic product formulation, so as to provide a uniform cosmetic. The present invention provides a cosmetic comprising the following components (A) and (B):
(A) ultrafine cellulose fibers having a fiber width of 1000 nm or less; and
(B) a water-soluble polymer.

12 Claims, 1 Drawing Sheet

(56) References Cited

FOREIGN PATENT DOCUMENTS

| JP | 2015-67573 A | 4/2015 |
|---|---|---|
| JP | 2015-151359 A | 8/2015 |
| JP | 2964727 A | 4/2016 |
| JP | 2018-511623 A | 4/2018 |
| WO | WO 00/47628 A2 | 8/2000 |
| WO | WO 00/47628 A3 | 8/2000 |
| WO | WO 2014/175289 A1 | 10/2014 |
| WO | WO 2014/185505 A1 | 11/2014 |
| WO | WO 2014/196357 A1 | 12/2014 |
| WO | WO 2015/107995 A1 | 7/2015 |
| WO | WO 2016/060120 A1 | 4/2016 |
| WO | WO 2016/166179 A1 | 10/2016 |

OTHER PUBLICATIONS

Canadian Office Action, dated Jul. 29, 2019, for corresponding Canadian Application No. 2,997,023.
Japanese Office Action, dated Sep. 10, 2019, for corresponding Japanese Application No. 2015-154035, with an English translation.
Japanese Office Action, dated Sep. 3, 2019, for corresponding Japanese Application No. 2015-172380, with an English translation.
Korean Office Action for Korean Application No. 10-2018-7006080, dated May 15, 2019, with an English translation.
Japanese Third Party Observation, dated Jan. 21, 2020, for Japanese Application No. 2015-172380.
Canadian Office Action, dated Feb. 14, 2020, for corresponding Canadian Application No. 2,997,023.
Japanese Office Action, dated Mar. 3, 2020, for corresponding Japanese Application No. 2015-154035, with machine translation.
Japanese Office Action, dated Mar. 31, 2020, for corresponding Japanese Application No. 2015-172380, with machine translation.
Korean Office Action, dated Mar. 31, 2020, for corresponding Korean Application No. 10-2018-7006080, with machine translation.
Chinese Office Action, dated May 22, 2020, for corresponding Chinese Application No. 201680045333.3, with machine translation.
Xie Cheng et al.; Optimization of Preparation Technology of Alkali Pretreated Reed Pulp Nano-cellulose; Chemistry and Industry of Forest Products, vol. 33, No. 1; Feb. 2013, with English abstract.
European Office Action, dated Sep. 9, 2020, for corresponding European Application No. 16 833 109.8.
Japanese Decision of Rejection, dated Oct. 27, 2020, for corresponding Japanese Application No. 2015-172380, with machine translation.
Korean Decision of Rejection, dated Sep. 28, 2020, for corresponding Korean Application No. 10-2018-7006080, with machine translation.
Notice of Third Party Observation, dated Aug. 18, 2020, for Japanese Application No. 2015-172380.
Korean Decision of Rejection, dated Dec. 10, 2020, for corresponding Korean Application No. 10-2018-7006080, with machine translation.
Trial Decision on Appeal aqainst Decision to Reject Application for corresponding Korean patent application No. 10-2018-7006080, dated Aug. 17, 2021, with English translation.
Japanese Notice of Third Party Observation issued in corresponding Japanese Application No. 2015-172380, dated Jun. 22, 2021, with partial English translation (Submission date of the Third Party Observation: May 13, 2021).
Japanese Notice of Third Party Observation issued in corresponding Japanese Application No. 2015-172380, dated Jun. 22, 2021, with partial English translation (Submission date of the Third Party Observation: May 26, 2021).
Korean Office Action for Korean Application No. 10-2021-7007510, dated May 24, 2021, with English translation.
Japanese Office Action for corresponding Japanese Palent Application No. 2020-147484, dated Oct. 26, 2021, with English translation.
Notice of Third Party Observation for corresponding Japanese Patent Application No. 2021-010953, dated Oct. 26, 2821, with English translation.
Japanese Office Action for corresponding Japanese Application No. 2021-010953, dated Feb. 22, 2022, with English translation.
Decision of Refusal, dated May 10, 2022, issued in coresponding Japanese Patent Application No. 2020-147484, with English Machine translation.

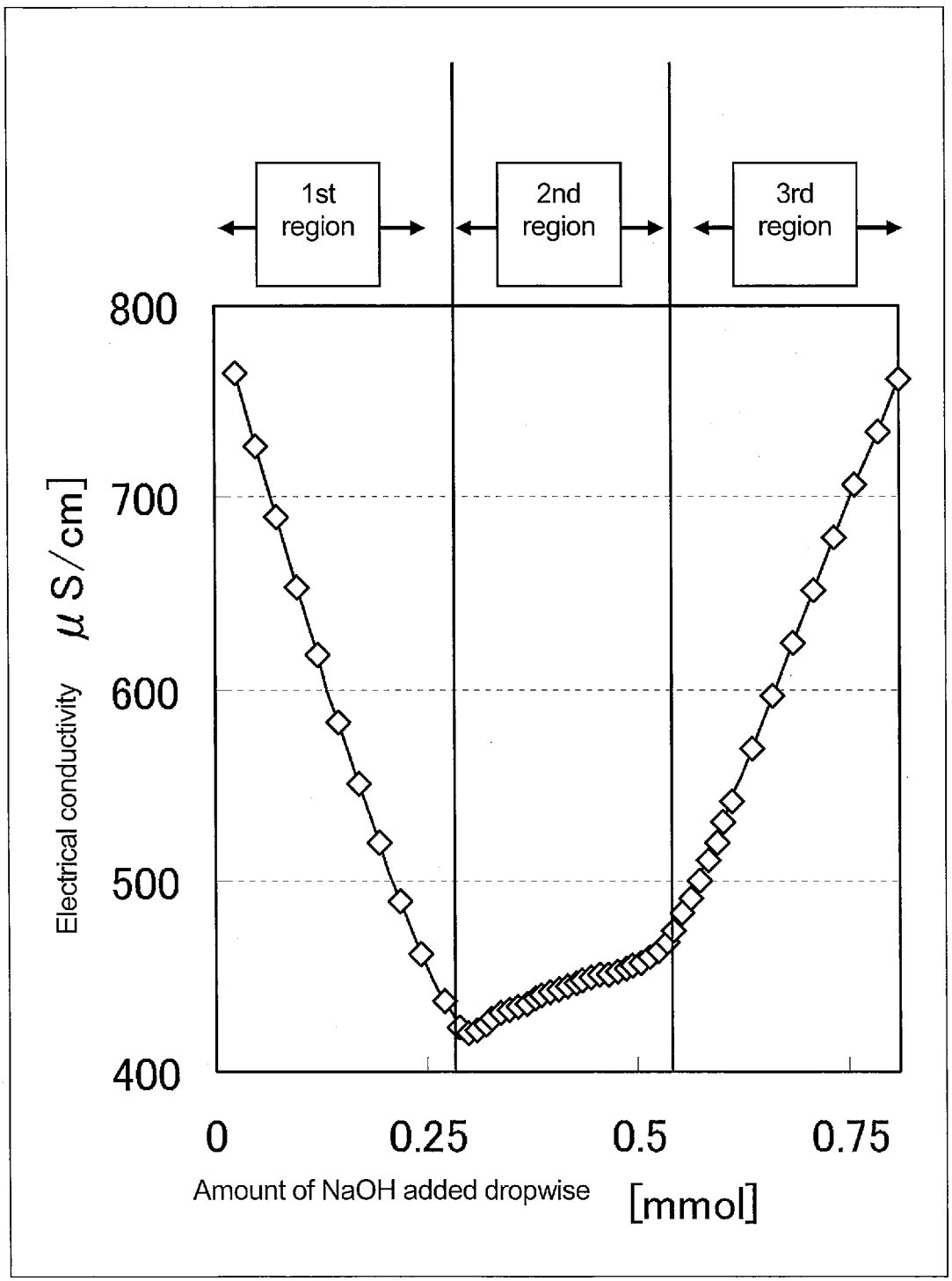

COSMETIC

TECHNICAL FIELD

The present invention relates to a cosmetic comprising ultrafine cellulose fibers and a water-soluble polymer.

BACKGROUND ART

In general, a cosmetic has a viscosity that is adjusted depending on purpose or intended use, and various thickeners or gelatinizers are used depending on the types of formulations. Specific examples of such thickeners or gelatinizers, which have been often used, include water-soluble polymers such as a carboxyvinyl polymer, xanthan gum, cellulose, guar gum, alginic acid, and polyacrylic acid. These thickeners or gelatinizers are appropriately used depending on intended use, and the mixed amount, mixed components and the like are changed, so that various cosmetics ranging from low-viscosity cosmetics such as a thickened lotion to solid gel-state cosmetics such as hair chick can be prepared.

Since a carboxyvinyl polymer and a salt thereof are able to form gel with a small amount thereof and are also able to be used in combination with an emulsifier, they have been frequently used in cosmetics. However, a gel structure formed with such a carboxyvinyl polymer has been problematic in that it is easily collapsed in the presence of salts, and also in that it is easily influenced by pH. In addition, there has been another problem that if the mixed amount of a thickener is increased in order to obtain a composition having a high viscosity, stickiness or twist appears upon application thereof. Moreover, a technique involving the combined use of alkylated starch, an alkyl methacrylate-acrylic acid copolymer, and the like, which are highly resistant to salts (Patent Document 1), has been known. However, such a method has been problematic in that the obtained product has a high gel hardness and is likely to become vulnerable.

It has been known that ultrafine cellulose fibers are used as one component of a gel composition. For example, Patent Document 2 discloses a dry composition, which has good dispersibility and improved stability as a result of addition of ultrafine cellulose fibers to a water-soluble polymer, and a thickening gelatinizer, a liquid composition and a gel composition, each of which comprises the dry composition. More specifically, Patent Document 2 discloses a dry composition consisting of 1% to 49% by mass of crystalline ultrafine cellulose fibers made from a plant cell wall as a raw material, and 51% to 99% by mass of a water-soluble polymer. Patent Document 2 describes that it is preferable to use carboxymethyl cellulose sodium and dextrin as water-soluble polymers. Patent Document 2 describes that the fiber width (minor axis) of a ultrafine fiber is 2 nm to 60 μm. However, the ultrafine cellulose fibers disclosed in Patent Document 2 includes a fiber width of a μm order, and thus, this ultrafine cellulose fibers are not composed of only fibers having a fiber width with a nm order size.

Patent Document 3 discloses a gel composition formed using cellulose fibers, which is characterized in that the content of the cellulose fibers is in the range of 0.3% to 5.0% by weight, based on the total weight of the gel composition. The cellulose fibers disclosed in Patent Document 3 have a maximum fiber diameter of 1000 nm or less and a number average fiber diameter of 2 to 150 nm, wherein the cellulose has 0.08 to 0.3 mmol/g of aldehyde groups and 0.6 to 2.0 mmol/g of carboxyl groups. Patent Document 4 discloses a viscous aqueous composition comprising cellulose fibers, a thickening promoter (which is selected from nonionic thickening polysaccharides, an acrylic polymer, and a cellulose derivative having a weight average molecular weight of 120000 or more), and water. The cellulose fibers disclosed in Patent Document 4 have a maximum fiber diameter of 1000 nm or less and a number average fiber diameter of 2 to 150 nm, and the rate of carboxyl groups in the cellulose is 0.6 to 2.0 mmol/g.

Since a dispersion composed of the cellulose fibers disclosed in Patent Document 3 and Patent Document 4 has a high thickening property, the use of such ultrafine cellulose fibers as a thickener for cosmetic products and the like has been proposed. Furthermore, Patent Document 5 describes that ultrafine cellulose fibers have moisturizing ability.

PRIOR ART DOCUMENTS

Patent Documents

Patent Document 1: JP 2000-327516 A
Patent Document 2: JP 2008-106178 A
Patent Document 3: JP 2010-37348 A
Patent Document 4: JP 2012-126788 A
Patent Document 5: JP 2011-56456 A

SUMMARY OF INVENTION

Object to be Solved by the Invention

When ultrafine cellulose fibers are intended to be used as a thickener for cosmetics, it has been problematic in that the thickening property of the ultrafine cellulose fibers cannot be sufficiently exhibited in cosmetic product formulations, or it causes agglutination or the like, because such cosmetic product formulations often comprise electrolytes such as salts. On the other hand, when such ultrafine cellulose fibers are not used as a thickener, but only a water-soluble polymer such as xanthan gum is used in cosmetic product formulations, such a water-soluble polymer has caused a problem that is the stickiness of cosmetics. Under the aforementioned circumstances, it has been desired to develop a cosmetic, which provides good feeling and realizes sufficient thickening effects and formulation stability, even in the coexistence of salts, powders, etc.

It is an object of the present invention to suppress agglutination of ultrafine cellulose fibers, while using the ultrafine cellulose fibers as a thickener in a cosmetic product formulation, so as to provide a uniform cosmetic.

Means for Solving the Object

In order to achieve the aforementioned object, the present inventors have conducted intensive studies regarding conditions for maintaining the high dispersibility of ultrafine cellulose fibers in a cosmetic product formulation. As a result, it has been revealed that a cosmetic, which achieves the aforementioned object, can be provided by using ultrafine cellulose fibers and also mixing a water-soluble polymer with the ultrafine cellulose fibers. The present invention has been completed based on the above-described findings.

The present invention includes the following invention.
(1) A cosmetic comprising the following components (A) and (B):
(A) ultrafine cellulose fibers having a fiber width of 1000 nm or less; and
(B) a water-soluble polymer.

(2) The cosmetic according to (1), wherein the component (B) comprises thickening polysaccharides.
(3) The cosmetic according to (2), wherein the component (B) comprises ionic thickening polysaccharides.
(4) The cosmetic according to any one of (1) to (3), wherein the component (A) is mixed in an amount of 0.01% to 2.0% by mass based on the mass of the entire cosmetic.
(5) The cosmetic according to any one of (1) to (4), wherein the component (B) is mixed in an amount of 0.03% to 1.0% by mass based on the mass of the entire cosmetic.
(6) The cosmetic according to any one of (1) to (5), which further comprises, as a component (C), one or two or more selected from the group consisting of inorganic powder, organic powder, inorganic acid, organic acid, inorganic acid salt, organic acid salt, and an anionic surfactant.
(7) A cellulose-containing composition for use in forming a cosmetic, wherein the cellulose-containing composition comprises the following components (A) and (B):
(A) ultrafine cellulose fibers having a fiber width of 1000 nm or less; and
(B) a water-soluble polymer.
(8) A cosmetic method which comprises applying, to living body, a cosmetic comprising the following components (A) and (B):
(A) ultrafine cellulose fibers having a fiber width of 1000 nm or less; and
(B) a water-soluble polymer.
(9) Use of the following components (A) and (B) for production of cosmetic:
(A) ultrafine cellulose fibers having a fiber width of 1000 nm or less; and
(B) a water-soluble polymer.

Advantageous Effects of Invention

The cosmetic of the present invention comprising ultrafine cellulose fibers and a water-soluble polymer has good uniformity as a product, no stickiness of the product, and good sense of use.

BRIEF DESCRIPTION OF DRAWINGS

FIG. 1 shows the relationship between the amount of NaOH added dropwise to a fiber raw material and the electrical conductivity.

EMBODIMENT OF CARRYING OUT THE INVENTION

Hereinafter, the present invention will be described in more detail. It is to be noted that explanation about materials, methods, numerical value ranges, and the like in the present description is not intended to limit the present invention to the explained materials, methods, numerical value ranges, and the like, and also that the explanation is not intended to exclude the use of other materials, other methods, other numerical value ranges, and the like.

The cosmetic of the present invention comprises the following components (A) and (B):
(A) ultrafine cellulose fibers having a fiber width of 1000 nm or less; and
(B) a water-soluble polymer.
<Ultrafine Cellulose Fibers>

Examples of a cellulose raw material include, but are not particularly limited to, paper pulp, cotton-based pulp such as cotton linter or cotton lint, non-wood-based pulp such as hemp, straw or bagasse, and cellulose isolated from sea squirts, seaweed, etc. Among these, paper pulp is preferable in terms of availability, but it is not particularly limited thereto. Examples of such paper pulp include broad-leaved tree bleached kraft pulp and needle-leaved tree bleached kraft pulp. Examples of the broad-leaved tree bleached kraft pulp include hardwood bleached kraft pulp (LBKP), hardwood unbleached kraft pulp (LUKP), and hardwood oxygen bleached kraft pulp (LOKP). Examples of the needle-leaved tree bleached kraft pulp include softwood bleached kraft pulp (NBKP), softwood unbleached kraft pulp (NUKP), and softwood oxygen bleached kraft pulp (NOKP). More examples of such paper pulp include chemical pulp, semi-chemical pulp, mechanical pulp, non-wood pulp, and deinked pulp in which waste paper is used as a raw material, but the examples are not particularly limited thereto. Examples of the chemical pulp include sulfite pulp (SP) and soda pulp (AP). Examples of the semi-chemical pulp include semichemical pulp (SCP) and chemiground wood pulp (CGP). Examples of the mechanical pulp include ground pulp (GP) and thermomechanical pulp (TMP, BCTMP). Examples of the non-wood pulp include those made from paper mulberry, mitsumata, hemp, kenaf, or the like, used as raw materials. Among these, in terms of availability, kraft pulp, deinked pulp, and sulfite pulp are preferable, but the examples are not particularly limited thereto. Such cellulose raw materials may be used as a single type alone, or may be used by mixing two or more thereof.

The average fiber width of ultrafine cellulose fibers (which is simply referred to as "ultrafine fibers" at times) is 1000 nm or less by observation under an electron microscope. The average fiber width is preferably 2 to 1000 nm, more preferably 2 to 100 nm, even more preferably 2 to 50 nm, and further preferably 2 nm to 10 nm, but is not particularly limited thereto. If the average fiber width of ultrafine cellulose fibers is less than 2 nm, the ultrafine cellulose fibers are dissolved in water in the form of cellulose molecules, and thus, the physical properties (strength, rigidity, and dimensional stability) of the ultrafine cellulose fibers cannot be expressed. Herein, whether the ultrafine cellulose fibers have a type I crystal structure can be identified using a diffraction profile obtained from a wide-angle X-ray diffraction image, in which CuKα (λ=1.5418 Å) monochromated with graphite is used. Specifically, the ultrafine cellulose fibers having a type I crystal structure can be identified based on the fact that they have typical peaks in two positions, namely, around 2θ=14 to 17° and around 2θ=22 to 23°. The ultrafine fibers of the present invention indicate monofibers having a fiber width of 1000 nm or less as a whole, and do not indicate thick fibers having a fiber width of larger than 1000 nm and also having a branched portion with a width of 1000 nm or less.

The measurement of the fiber width of the ultrafine cellulose fibers by observation under an electron microscope is carried out as follows. An aqueous suspension containing 0.05% to 0.1% by mass of cellulose fibers is prepared, and the prepared suspension is then casted on a carbon film-coated grid that has been subjected to a hydrophilic treatment, so as to produce a sample for TEM observation. When the sample comprises wide fibers, the SEM image on the surface of a glass, on which the sample has been casted, may be observed. The sample is observed by electron microscopy imaging at a magnification of 1000, 5000, 10000, or 50000, depending on the width of fibers constituting the sample. However, the sample, observation conditions, and magnification are adjusted, such that they satisfy the following conditions.

(1) A single straight line X is drawn in any given portion in an observation image, and 20 or more fibers intersect with the straight line X.
(2) A straight line Y, which intersects perpendicularly with the aforementioned straight line in the same image as described above, is drawn, and 20 or more fibers intersect with the straight line Y.

The width of a fiber intersecting with the straight line X and the straight line Y in an observation image satisfying the above-described conditions is read by visual observation. Thus, 3 or more images of surface portions, which are not at least overlapped, are observed, and the width of a fiber intersecting the straight line X and the straight line Y is read in each image. Hence, at least 120 fiber widths (20 fibers× 2×3=120) are read. The average fiber width (which is simply referred to as a "fiber width" at times) of cellulose fibers indicates an average value of the thus read fiber widths.

The fiber length of ultrafine cellulose fibers is not particularly limited. It is preferably 0.1 to 1000 μm, more preferably 0.1 to 800 μm, and particularly preferably 0.1 to 600 μm. If the fiber length is less than 0.1 μm, the crystal region of ultrafine cellulose fibers is destroyed, and thus, the original physical properties cannot be exhibited. On the other hand, if the fiber length exceeds 1000 μm, the slurry viscosity of ultrafine fibers becomes extremely high, and thus, it becomes difficult to handle it. The fiber length can be obtained by an image analysis involving TEM, SEM, or AFM.

The rate of a crystal portion comprised in ultrafine cellulose fibers is not particularly limited in present invention. It is preferable to use cellulose, in which the crystallinity obtained by an X-ray diffractometry is 60% or more. The crystallinity is preferably 65% or more, and more preferably 70% or more. In this case, more excellent performance can be expected, in terms of heat resistance and the expression of low linear thermal expansion. The crystallinity can be obtained by measuring an X-ray diffraction profile and obtaining it from its pattern according to a common method (Seagal et al., Textile Research Journal, Vol. 29, p. 786, 1959).

<Chemical Treatment>

In the present invention, the ultrafine cellulose fibers can be, for example, ultrafine cellulose fibers having an ionic substituent, which is obtained by performing a chemical treatment and a defibration treatment on a cellulose raw material. Such ultrafine cellulose fibers having an ionic substituent are preferable because it can be converted to ultrafine fibers by electrostatic repulsion effects. Such ultrafine cellulose fibers having a substituent are not agglutinated in water as a result of electrostatic repulsion effects, and it can be stable. On the other hand, the effects are weakened in water containing salts, and it becomes difficult to stably disperse the ultrafine cellulose fibers. Thus, the present invention is particularly suitable to stabilize ultrafine cellulose fibers even in water containing salts and to exhibit thickening effects. The ultrafine cellulose fibers used in the present invention can comprise, for example, either one of or both of a cationic substituent and an anionic substituent. Examples of the anionic substituent include a carboxyl group, a sulfone group, and a phosphoric acid group. Examples of the cationic substituent include groups having onium such as ammonium, phosphonium or sulfonium. In the present invention, from the viewpoint of suppressing formulation stability or stickiness, the ultrafine cellulose fibers preferably comprise, as an ionic substituent, one or two or more selected from a phosphoric acid group, a carboxyl group and a sulfone group, more preferably comprises at least one of a phosphoric acid group and a carboxyl group, and particularly preferably comprises a phosphoric acid group. By using ultrafine cellulose fibers having such characteristics, a more uniform formulation can be obtained as a cosmetic. On the other hand, such ultrafine cellulose fibers can also be obtained, for example, by performing a defibration treatment, without introduction of an ionic substituent by a chemical treatment. In this case, it becomes possible to reduce the production cost of cosmetics.

[General Chemical Treatment]

The chemical treatment method of a cellulose raw material is not particularly limited, as long as it is a method capable of obtaining ultrafine fibers. Examples of such a chemical treatment method include an acid treatment, an ozone treatment, a TEMPO oxidation treatment, an enzyme treatment, and a treatment of using a compound capable of forming a covalent bond with a functional group in cellulose or fiber raw material, but are not limited thereto. In addition, when ultrafine cellulose fibers have a phosphoric acid-derived substituent, it is preferable to, for example, treat the ultrafine cellulose fibers with a compound having a phosphoric acid or/and a salt thereof, as a chemical treatment method.

An example of the acid treatment is the method described in Otto van den Berg; Jeffrey R. Capadona; Christoph Weder; Biomacromolecules 2007, 8, 1353-1357, but the example of the acid treatment is not particularly limited thereto. Specifically, cellulose fibers are treated by hydrolysis using sulfuric acid, hydrochloric acid, etc.

An example of the ozone treatment is the method described in JP 2010-254726 Å, but the example of the ozone treatment is not particularly limited thereto. Specifically, fibers are treated with ozone and are then dispersed in water, and the thus obtained aqueous dispersion of fibers is subjected to a crushing treatment.

An example of the TEMPO oxidation treatment is the method described in Saito T & al., Homogeneous suspensions of individualized ultrafine fibers from TEMPO-catalyzed oxidation of native cellulose. Biomacromolecules 2006, 7 (6), 1687-91, but the example of the TEMPO oxidation treatment is not particularly limited thereto. Specifically, fibers are subjected to a TEMPO oxidation treatment and are then dispersed in water, and the thus obtained aqueous dispersion of fibers is subjected to a crushing treatment.

An example of the enzyme treatment is the method described in WO 2013/176033 (the content described in WO 2013/176033 is cited herein by reference in its entirety), but the example of the enzyme treatment is not particularly limited thereto. Specifically, this is a method of treating a fiber raw material with enzyme under conditions in which the ratio between the EG activity of the enzyme and the CBHI activity thereof is 0.06 or more.

The EG activity is measured and defined as follows.

A substrate solution (containing an acetic acid-sodium acetate buffer with a concentration of 100 mM and pH 5.0) of 1% (W/V) carboxymethyl cellulose (CMCNa, High viscosity; Cat No150561, MP Biomedicals, Inc.) is prepared. A measurement enzyme has been previously diluted with a buffer (the same as described above) (wherein the dilution magnification may be set, such that the absorbance of the following enzyme solution may be in a calibration curve obtained from the following glucose standard solution). 10 μl of the enzyme solution obtained as a result of the aforementioned dilution is added to 90 μl of the substrate solution, and the obtained mixture is then reacted at 37° C. for 30 minutes.

In order to prepare a calibration curve, ion exchange water (blank) and glucose standard solutions (at least four standard solutions having different concentrations selected from the concentration range of 0.5 to 5.6 mM) are selected, and individual solutions are prepared in amounts of 100 µl each, followed by incubation at 37° C. for 30 minutes.

300 µl of a DNS coloring solution (1.6% by mass of NaOH, 1% by mass of 3,5-dinitrosalicylic acid, and 30% by mass of potassium sodium tartrate) is added to each of the enzyme-containing solution after completion of the above-described reaction, a blank for calibration curve, and glucose standard solutions, and the obtained mixtures are each boiled for 5 minutes, so that the solutions become colored. Immediately after coloration, the solutions are cooled on ice, and 2 ml of ion exchange water is then added to the reaction solutions, followed by fully mixing. The mixed solutions are each left at rest for 30 minutes, and the absorbance is then measured within 1 hour.

For the measurement of absorbance, 200 µl of the solution is dispensed in a 96-well microwell plate (e.g., 269620, manufactured by NUNC), and the absorbance at 540 nm can be then measured using a microplate reader (e.g., infinite M200, manufactured by TECAN).

Using the absorbance of each glucose standard solution, from which the absorbance of the blank has been subtracted, and a glucose concentration, a calibration curve is produced. The glucose equivalent amount in the enzyme solution is obtained by subtracting the absorbance of the blank from the absorbance of the enzyme solution and then calculating it using the calibration curve (in a case where the absorbance of the enzyme solution cannot be in the calibration curve, the dilution magnification used upon the dilution of the enzyme with the aforementioned buffer is changed, and the measurement is carried out again). The amount of enzyme necessary for the generation of 1 µmole of reducing sugar such as glucose per minute is defined as 1 unit, and the EG activity can be obtained according to the following formula.

EG activity=glucose equivalent amount(µmole) in 1 ml of enzyme solution obtained by dilution with buffer/30 minutes×dilution magnification

[See Sakuzo FUKUI, "*Seibutsu Kagaku Jikken Ho (Kangento no Teiryo Ho)*, (Biochemistry Experimental Methods (Methods for quantifying reducing sugars)), 2nd edition," Gakkai Shuppan Center, pp. 23-24, (1990)].

The CBHI activity is measured and defined as follows. 32 µl of 1.25 mM 4-methylumberiferyl-cellobioside (dissolved in an acetic acid-sodium acetate buffer with a concentration of 125 mM and pH 5.0) is dispensed in a 96-well microwell plate (e.g., 269620, manufactured by NUNC). Thereafter, 4 µl of 100 mM glucono-1,5-lactone is added to the plate, and 4 µl of a measurement enzyme solution diluted with the same buffer as described above (wherein the dilution magnification may be set, such that the fluorescence degree of the following enzyme solution may be in a calibration curve obtained from the following glucose standard solution) is further added thereto, followed by performing a reaction at 37° C. for 30 minutes. Thereafter, 200 µl of a 500 mM glycine-NaOH buffer (pH 10.5) is added to the reaction mixture, so that the reaction is terminated.

40 µl each of 4-methyl-umberiferon standard solutions (at least four standard solutions having different concentrations selected from the concentration range of 0 to 50 µM) used as calibration curve standard solutions is dispensed in the same 96-well microwell plate as described above, and it is then incubated at 37° C. for 30 minutes. Thereafter, 200 µl of a 500 mM glycine-NaOH buffer (pH 10.5) is added thereto.

Using a microplate reader (e.g., FluoroskanAscent FL, manufactured by Thermo-Labsystems), the fluorescence degree is measured at 350 nm (excitation light: 460 nm). Using a calibration curve produced from the data of standard solutions, the amount of 4-methyl-umberiferon generated in the enzyme solution is calculated (in a case where the fluorescence degree of the enzyme solution cannot be in the calibration curve, the dilution magnification is changed and the measurement is then carried out again). The amount of the enzyme necessary for the generation of 1 µmol of 4-methyl-umberiferon per minute is defined as 1 unit, and the CBHI activity can be obtained according to the following formula.

CBHI activity=amount(µmole) of 4-methyl-umberiferon generated in 1 ml of enzyme solution after dilution/30 minutes×dilution magnification An example of the treatment of using a compound capable of forming a covalent bond with a functional group in cellulose or fiber raw material is the following method, but is not particularly limited thereto:

The method of using "at least one compound selected from among oxoacid and polyoxoacid, which contain a phosphorus atom in the structure thereof, and a salt thereof" described in International Publication WO 2013/073652 (PCT/JP2012/079743).

The method of introducing a cationic substituent into cellulose fibers is, for example, a method of treating a cellulose fiber raw material with a cationization agent. In the present invention, a cationic substituent can be introduced into cellulose fibers, for example, by adding a cationization agent and an alkali compound to the cellulose fibers, so that they are allowed to react with the cellulose fibers. Examples of the cationization agent that can be used herein include those having a quaternary ammonium group and a group reacting with the hydroxy group of cellulose. Examples of the group reacting with the hydroxy group of cellulose include an epoxy group, a functional group having the structure of halohydrin, a vinyl group, and a halogen group. Specific examples of the cationization agent that can be used herein include glycidyltrialkylammonium halide such as glycidyltrimethylammonium chloride or 3-chloro-2-hydroxypropyltrimethylammonium chloride, and the halohydrin-type compounds thereof. Examples of the alkali compound include: inorganic alkali compounds, such as hydroxides of alkaline metals or alkaline-earth metals, carbonates of alkaline metals or alkaline-earth metals, or phosphates of alkaline metals or alkaline-earth metals; and organic alkali compounds, such as ammonia, aliphatic amine, aromatic amine, aliphatic ammonium, aromatic ammonium, a heterocyclic compound or a hydroxide thereof, carbonate, or phosphate.

The amount of an ionic substituent introduced is not particularly limited. It is, for example, 0.1 to 3.0 mmol/g, preferably 0.14 to 2.5 mmol/g, more preferably 0.2 to 2.0 mmol/g, and particularly preferably 0.2 to 1.8 mmol/g, based on 1 g (mass) of ultrafine cellulose fibers. By setting the amount of the ionic substituent introduced at the above-described lower limit value or more, formation of ultrafine fibers from the ultrafine cellulose fibers becomes easier, and the stability of the ultrafine cellulose fibers can be improved. On the other hand, by setting the amount of the ionic substituent introduced at the above-described upper limit value or less, it becomes possible to impart more preferred viscosity to the cosmetic. Besides, in the present invention, for example, an aspect of not introducing carboxyl groups can be adopted. In this case, the content of carboxyl groups comprised as ionic substituents in the ultrafine cellulose fibers can be set at, for example, 0.05 mmol/g or less. Moreover, in the present invention, for example, an aspect of not introducing phosphoric acid groups can also be adopted. In this case, the content of phosphoric acid groups comprised as ionic substituents in the ultrafine cellulose fibers can be set at, for example, 0.05 mmol/g or less.

[Introduction of Phosphoric Acid Group]

In the present invention, the ultrafine cellulose fibers have, for example, a phosphoric acid-derived substituent (which is simply referred to as a "phosphoric acid group" at times in the present description), such as a phosphoric acid ester group.

Hereafter, phosphoric acid esterification will be described.

(Phosphoric Acid Group Introduction Step)

The phosphoric acid group introduction step is a step of allowing a compound having a phosphoric acid group or/and a salt thereof (hereinafter, referred to as "compound A") to react with the fiber raw material including cellulose. This reaction may be carried out in the presence of urea or/and a derivative thereof (hereinafter, referred to as "compound B"). Thereby, the phosphoric acid group can be introduced into a hydroxy group in the cellulose fibers, but the phosphoric acid group introduction step is not particularly limited thereto.

The phosphoric acid group introduction step inevitably comprises the step of introducing a phosphoric acid group into cellulose and may comprise, as desired, an alkali treatment step mentioned later, a step of washing off redundant reagents, etc.

One example of the method for allowing compound A to act on the fiber raw material in the presence of compound B includes a method of mixing the fiber raw material in a dry or wet state with a powder or an aqueous solution of compound A and compound B. Another example thereof includes a method of adding a powder or an aqueous solution of compound A and compound B to slurry of the fiber raw material. Among them, a method of adding an aqueous solution of compound A and compound B to the fiber raw material in a dry state, or a method of adding a powder or an aqueous solution of compound A and compound B to the fiber raw material in a wet state is preferable because of the high homogeneity of the reaction, though the method is not particularly limited thereto. Compound A and compound B may be added at the same time or may be added separately. Alternatively, compound A and compound B to be subjected to the reaction may be first added as an aqueous solution, which is then compressed to squeeze out redundant chemicals. The form of the fiber raw material is preferably a cotton-like or thin sheet form, though the form is not particularly limited thereto.

The compound A used in the present embodiment is a compound having a phosphoric acid group or/and a salt thereof.

Examples of the compound having a phosphoric acid group include, but are not particularly limited to, phosphoric acid, lithium salts of phosphoric acid, sodium salts of phosphoric acid, potassium salts of phosphoric acid, and ammonium salts of phosphoric acid. Examples of the lithium salts of phosphoric acid include lithium dihydrogen phosphate, dilithium hydrogen phosphate, trilithium phosphate, lithium pyrophosphate, and lithium polyphosphate. Examples of the sodium salts of phosphoric acid include sodium dihydrogen phosphate, disodium hydrogen phosphate, trisodium phosphate, sodium pyrophosphate, and sodium polyphosphate. Examples of the potassium salts of phosphoric acid include potassium dihydrogen phosphate, dipotassium hydrogen phosphate, tripotassium phosphate, potassium pyrophosphate, and potassium polyphosphate. Examples of the ammonium salts of phosphoric acid include ammonium dihydrogen phosphate, diammonium hydrogen phosphate, triammonium phosphate, ammonium pyrophosphate, and ammonium polyphosphate.

Among them, phosphoric acid, a sodium salt of phosphoric acid, a potassium salt of phosphoric acid, or an ammonium salt of phosphoric acid is preferable from the viewpoint of the high efficiency of phosphoric acid group introduction, higher improvement in defibration efficiency in a defibration step described below, low cost, and industrial applicability. Sodium dihydrogen phosphate or disodium hydrogen phosphate is more preferable, though the compound A is not particularly limited thereto.

The compound A is preferably used as an aqueous solution because of the enhanced homogeneity of the reaction and the increased efficiency of phosphoric acid group introduction, though the form is not particularly limited thereto. The pH of the aqueous solution of the compound A is not particularly limited, and is preferably 7 or lower because of the increased efficiency of phosphoric acid group introduction, more preferably 3 to 7 from the viewpoint of suppressing the hydrolysis of pulp fibers. The pH may be adjusted, for example, by using an acidic compound having a phosphoric acid group and an alkaline compound having a phosphoric acid group in combination and changing the ratio between their amounts. Alternatively, the pH may be adjusted, for example, by adding an inorganic alkali or an organic alkali to an acidic compound having a phosphoric acid group.

The amount of the compound A added to the fiber raw material is not particularly limited. When the amount of the compound A added is converted to the amount of a phosphorus atom, the amount of the phosphorus atom added to the fiber raw material is preferably 0.5% to 100% by mass, more preferably 1% to 50% by mass, most preferably 2% to 30% by mass. When the amount of the phosphorus atom added to the fiber raw material falls within the range of 0.5% to 100% by mass, the yield of the ultrafine cellulose fibers can be further improved. If the amount of the phosphorus atom added to the fiber raw material exceeds 100% by mass, this is not preferable because the effect of improving the yield levels off and cost of the compound A used is elevated. On the other hand, if the amount of the phosphorus atom added to the fiber raw material is lower than 0.5% by mass, this is not preferable because an adequate yield cannot be obtained.

Examples of the compound B used in the present embodiment include, but are not particularly limited to, urea, thiourea, biuret, phenyl urea, benzyl urea, dimethyl urea, diethyl urea, tetramethyl urea, benzoylene urea, and hydantoin. Among them, urea is preferable because it is inexpensive, is easily handled, and easily forms a hydrogen bond with the fiber raw material having a hydroxyl group.

The compound B, as with the compound A, is preferably used as an aqueous solution, though the form is not particularly limited thereto. An aqueous solution containing both of the compound A and the compound B dissolved therein is preferably used because of the enhanced homogeneity of the reaction, though the form is not particularly limited thereto.

The amount of the compound B added to the fiber raw material is not particularly limited, and is preferably 1% to 300% by mass.

The reaction system may contain an amide or an amine, in addition to the compound A and the compound B. Examples of the amide include formamide, dimethylformamide, acetamide, and dimethylacetamide. Examples of the amine include methylamine, ethylamine, trimethylamine, triethylamine, monoethanolamine, diethanolamine, triethanolamine, pyridine, ethylenediamine, and hexamethylenediamine. Among them, particularly, triethylamine is known to work as a favorable reaction catalyst.

(Amount of Phosphoric Acid-Derived Substituent Introduced)

The amount of a phosphoric acid-derived substituent introduced is 0.1 mmol/g or more and 3.0 mmol/g or less, preferably 0.14 mmol/g or more and 2.5 mmol/g or less, and more preferably 0.2 mmol/g or more and 2.0 mmol/g or less, based on 1 g (mass) of the ultrafine cellulose fibers. The amount of the phosphoric acid-derived substituent introduced is further preferably 0.2 mmol/g or more and 1.8 mmol/g or less, particularly preferably 0.4 mmol/g or more and 1.8 mmol/g or less, and most preferably 0.6 mmol/g or more and 1.8 mmol/g or less. By setting the amount of the phosphoric acid-derived substituent introduced at the above-described lower limit value or more, formation of ultrafine fibers from the fiber raw material becomes easy, and the stability of the ultrafine cellulose fibers can be improved. On the other hand, by setting the phosphoric acid-derived substituent introduced at the above-described upper limit value or less, it becomes easier to impart preferred viscosity to the cosmetic.

The amount of the phosphoric acid-derived substituent introduced into the fiber raw material can be measured by a conductometric titration method. Specifically, ultrafine fiber formation is carried out by a defibration treatment step, the obtained ultrafine cellulose fibers-containing slurry is then treated with an ion exchange resin, and a change in the electrical conductivity is then obtained while adding a sodium hydroxide aqueous solution thereto, so that the introduced amount can be measured.

The conductometric titration confers a curve shown in FIG. 1, as an alkali is added. First, the electrical conductivity is abruptly reduced (hereinafter, this region is referred to as a "first region"). Then, the conductivity starts to rise slightly (hereinafter, this region is referred to as a "second region"). Then, the increment of the conductivity is increased (hereinafter, this region is referred to as a "third region"). In short, three regions appear. The amount of the alkali required for the first region among these regions is equal to the amount of a strongly acidic group in the slurry used in the titration. The amount of the alkali required for the second region is equal to the amount of a weakly acidic group in the slurry used in the titration. When the condensation of the phosphoric acid group occurs, the weakly acidic group is apparently lost so that the amount of the alkali required for the second region is decreased as compared with the amount of the alkali required for the first region. On the other hand, the amount of the strongly acidic group agrees with the amount of the phosphorus atom regardless of the presence or absence of condensation. Therefore, the simple term "amount of the phosphoric acid group introduced (or amount of the phosphoric acid group)" or "amount of the substituent introduced (or amount of the substituent)" refers to the amount of the strongly acidic group.

(Alkali Treatment)

In the case of producing the phosphorylated ultrafine fibers, an alkali treatment can be performed between the phosphoric acid group introduction step and a defibration treatment step mentioned later. Examples of the alkali treatment method include, but are not particularly limited to, a method of immersing the phosphoric acid group-introduced fibers in an alkali solution.

The alkali compound contained in the alkali solution is not particularly limited, and may be an inorganic alkali compound or may be an organic alkali compound. The solvent in the alkali solution may be water or an organic solvent, and is not particularly limited. The solvent is preferably a polar solvent (water or a polar organic solvent such as an alcohol), more preferably an aqueous solvent containing at least water.

Among these alkali solutions, a sodium hydroxide aqueous solution or an aqueous potassium hydroxide solution is particularly preferable because of high versatility, though the alkali solution is not particularly limited thereto.

The temperature of the alkali solution in the alkali treatment step is not particularly limited, and is preferably 5° C. to 80° C., and more preferably 10° C. to 60° C.

The immersion time in the alkali solution in the alkali treatment step is not particularly limited, and is preferably 5 to 30 minutes, and more preferably 10 to 20 minutes.

The amount of the alkali solution used in the alkali treatment is not particularly limited, and is preferably 100% to 100000% by mass, and more preferably 1000% to 10000% by mass, with respect to the absolute dry mass of the phosphoric acid-introduced fibers.

In order to decrease the amount of the alkali solution used in the alkali treatment step, the phosphoric acid group-introduced fibers may be washed with water or an organic solvent before the alkali treatment step. After the alkali treatment, it is preferable for improving handlability to wash the alkali-treated phosphoric acid group-introduced fibers with water or an organic solvent before the defibration treatment step, though the method is not particularly limited thereto.

<Defibration Treatment>

The above-obtained ultrafine fibers can be defibrated in a defibration treatment step. In such a defibration treatment step, in general, using a defibration treatment device, a defibration treatment is performed on fibers, so as to obtain ultrafine fiber-containing slurry. The treatment device and the treatment method are not particularly limited.

Examples of the defibration treatment device that can be used herein include a high-speed defibrating machine, a grinder (a stone mortar type pulverizer), a high-pressure homogenizer, an ultra-high-pressure homogenizer, a high-pressure collision type pulverizer, a ball mill, and a bead mill. Moreover, other examples of the defibration treatment device that can be used herein include a disc-type refiner, a conical refiner, a twin-screw kneader, a vibration mill, a homomixer under high speed rotation, an ultrasonic dispersing machine, and a wet milling device such as a beater. Examples of the defibration treatment device are not limited thereto.

Examples of a preferred defibration treatment method include, but are not particularly limited to, a high-speed defibrating machine, a high-pressure homogenizer, and an ultra-high-pressure homogenizer, which are hardly influenced by crushing media, and cause a few problems regarding contamination.

Upon the defibration treatment, it is preferable to dilute the fiber raw material with a single use of water or an organic solvent, or with a combination thereof, so as to prepare a slurry, but the defibration treatment method is not particularly limited thereto. As a dispersion medium, a polar organic solvent, as well as water, can be used. Examples of a preferred polar organic solvent include, but are not particularly limited to, alcohols, ketones, ethers, dimethyl sulfoxide (DMSO), dimethylformamide (DMF), and dimethylacetamide (DMAc). Examples of the alcohols include methanol, ethanol, n-propanol, isopropanol, n-butanol, and t-butyl alcohol. Examples of the ketones include acetone and methyl ethyl ketone (MEK). Examples of the ethers include diethyl ether and tetrahydrofuran (THF). Such dispersion media may be used as a single type alone, or in combination of two or more types. Moreover, solids other than the fiber raw material, such as hydrogen-bound urea, may also be comprised in the dispersion media.

The ultrafine cellulose fibers used as a component (A) are mixed into a cosmetic, in an amount of preferably 0.01% to 2.0% by mass, more preferably 0.05% to 1.0% by mass, and particularly preferably 0.1% to 0.8% by mass, based on the mass of the entire cosmetic. Thereby, it becomes possible to contribute to the improvement of formulation stability or suppression of stickiness.

<Water-Soluble Polymer>

A water-soluble polymer is mixed into the cosmetic of the present invention, in order to stably disperse ultrafine cellulose fibers in the cosmetic. It is considered that such a water-soluble polymer prevents agglutination of the ultrafine cellulose fibers and stably disperses it in a liquid, as a result of steric hindrance caused by the swelling action thereof.

Examples of the water-soluble polymer include a carboxyvinyl polymer, an alkyl methacrylate-acrylic acid copolymer, and thickening polysaccharides. The water-soluble polymer is preferably thickening polysaccharides, more preferably ionic thickening polysaccharides, and even more preferably anionic thickening polysaccharides. Specifically, the thickening polysaccharides used in the present invention are not particularly limited, as long as they are thickening type polysaccharides. Specific examples of the thickening polysaccharides include xanthan gum, carrageenan, guar gum, locust bean gum, tamarind gum, glucomannan, cationized starch, cationized guar gum, quince seed, agar, methyl cellulose, hydroxyethyl cellulose, hydroxypropylmethylcellulose stearoxy ether, and carboxymethyl cellulose. Among these, xanthan gum is most preferable from the viewpoint of thickening property, dispersibility, and sense of use. Only one type of water-soluble polymer may be used, or two or more types of water-soluble polymers may be mixed with one another and may be then used. The amount of the water-soluble polymer mixed into the cosmetic as a whole is preferably 0.03% to 1.0% by mass, more preferably 0.06% to 0.8% by mass, and particularly preferably 0.08% to 0.5% by mass or less.

Moreover, from the viewpoint of contribution to the improvement of formulation stability and suppression of stickiness, the ratio $C_2/C_1$ of the content $C_2$ of the ultrafine cellulose fibers to the content $C_1$ of the water-soluble polymer comprised in the cosmetic is, for example, 0.1 or more and 30 or less, more preferably 1.0 or more and 20 or less, and particularly preferably 2 or more and 10 or less. In the present invention, an example of a preferred aspect can be a case where $C_2/C_1$ is 4 or more.

[Other Components]

The cosmetic of the present invention may further comprise, as another component (C), one or two or more selected from the group consisting of inorganic powder, organic powder, inorganic acid, organic acid, inorganic acid salt, organic acid salt, and an anionic surfactant, in addition to the above-described component (A) and component (B).

Examples of the inorganic powder include metal oxide, metal sulfate, talc, mica, kaoline, sericite, various types of mica, silicic acid and a silicic acid compound, tungsten acid metal salt, hydroxyapatite, vermiculite, higilite, and bentonite. Further examples of the inorganic powder include montmorillonite, hectorite, zeolite, ceramics powder, dibasic calcium phosphate, alumina, aluminum hydroxide, boron nitride, silicon nitride, boron nitride, and a silica compound.

Examples of the metal oxide include titanium oxide, zirconium oxide, zinc oxide, cerium oxide, and magnesium oxide.

Examples of the metal sulfate include barium sulfate, calcium sulfate, magnesium sulfate, calcium carbonate, and magnesium carbonate.

Examples of the mica include white mica, synthetic mica, gold mica, red mica, biotite, and lepidolite.

Examples of the silicic acid and the silicic acid compound include silicic acid, anhydrous silicic acid, aluminum silicate, magnesium silicate, aluminum magnesium silicate, calcium silicate, barium silicate, and strontium silicate.

The above-described specific examples of the inorganic powder are only several examples, and thus, the inorganic powder used herein is not limited thereto.

Only one type of inorganic powder may be used alone, or two or more types of inorganic powders may also be used in combination.

The amount of the inorganic powder mixed into the cosmetic as a whole is not particularly limited. In general, it is preferably 1.0% to 30.0% by mass. When the inorganic powder is added as an ultraviolet inhibitor to the cosmetic, the amount of the inorganic powder mixed into the cosmetic as a whole is, for example, set at preferably 5.0% by mass or more, and more preferably 10% by mass or more. Even in a case where the cosmetic comprises such a large amount of inorganic powder, according to the present invention, a cosmetic excellent in terms of stability can be obtained.

Examples of the organic powder include the following:

polyamide powder, polyacrylic acid-acrylic acid ester powder, polyester powder, polyethylene powder, polypropylene powder, polystyrene powder, polyurethane powder, benzoguanamine powder, and polymethyl benzoguanamine powder;

tetrafluoroethylene powder, polymethyl methacrylate powder, cellulose powder, silk powder, and nylon powders such as nylon 12 or nylon 6;

crosslinked silicone fine particles having a structure involving the crosslinking of dimethylpolysiloxane, crosslinked spherical polymethylsilsesquioxane fine particles, and fine particles formed by covering the surface of crosslinked spherical organopolysiloxane rubber with polymethylsilsesquioxane particles; and hydrophobic silica, a styrene-acrylic acid copolymer, a divinylbenzene-styrene copolymer, a vinyl resin, a urea resin, a phenol resin, a fluorine resin, a silicon resin, an acrylic resin, a melamine resin, an epoxy resin, and a polycarbonate resin.

The above-described specific examples of the organic powder are only several examples, and thus, the organic powder used herein is not limited thereto.

Only one type of organic powder may be used alone, or two or more types of organic powders may also be used in combination.

The amount of the organic powder mixed into the cosmetic as a whole is not particularly limited. In general, it is preferably 1.0% to 10.0% by mass.

Examples of the inorganic acid and inorganic acid salt include edetic acid and the salt thereof, sodium chloride, potassium chloride, potassium hydroxide, sodium hydroxide, and phosphoric acid and the salt thereof.

The amount of the inorganic acid and inorganic acid salt mixed into the cosmetic as a whole is not particularly limited. In general, it is preferably 0.01% to 10.0% by mass.

Examples of the organic acid and organic acid salt include citric acid, kojic acid, malic acid, triethanolamine, diisopropanolamine, glycolic acid, dipotassium glycyrrhizinate, and tranexamic acid, and the like. The amount of the organic acid and organic acid salt mixed into the cosmetic as a whole is not particularly limited. In general, the amount of the organic acid and organic acid salt mixed is preferably 0.01% to 10.0% by mass, and more preferably, dipotassium glycyrrhizinate is mixed in an amount of 0.05% to 0.30% by mass, and a chelating agent is mixed in an amount of 0.05% to 0.50% by mass, into the cosmetic.

Specific examples of the anionic surfactant include the following:

fatty acid soaps, such as sodium stearate, potassium stearate, triethanolamine stearate, sodium palmitate, potassium palmitate, triethanolamine palmitate, sodium laurate, potassium laurate, and triethanolamine laurate;

alkyl ether carboxylate and the salt thereof, condensate salt of amino acid and fatty acid, alkanesulfonate, alkenesulfonate, sulfonate of fatty acid ester, sulfonate of fatty acid amide, formalin condensation sulfonate, and alkyl sulfate ester salt;

sulfuric acid ester salts, such as higher secondary alcohol sulfuric acid ester salt, alkyl and allyl ether sulfuric acid ester salt, sulfuric acid ester salt of fatty acid ester, sulfuric acid ester salt of fatty acid alkylolamide, and sulfuric acid ester salts such as Turkey red oil, alkyl phosphate, and ether phosphate; and alkyl allyl ether phosphate, amide phosphate, N-acyl lactate, N-acyl sarcosine salt, and N-acyl amino acid activator.

The amount of the anionic surfactant mixed into the cosmetic as a whole is not particularly limited. In general, it is preferably 0.01% to 10.0% by mass, and more preferably 0.05% to 3.0% by mass.

<Method for Preparing Cosmetic>

A method for preparing the cosmetic of the present invention can be selected, as appropriate, depending on the types of components used, etc., and is not particularly limited. In the case of using water-soluble components and oil-soluble components, a water phase is mixed with an oil phase, so that the cosmetic of the present invention can be prepared. For example, a water phase containing water-soluble components has been prepared, individual components contained in the water phase have been dissolved by heating, and the components have previously been dispersed uniformly. Then, the thus prepared water phase is mixed with an oil phase (containing oil components) that has been adjusted to a suitable temperature, and the obtained mixture is then emulsified using a homogenizer or the like, so that the cosmetic of the present invention can be produced.

<Form of Cosmetic>

Specific examples of the cosmetic of the present invention include cosmetics for skin, make-up cosmetics, cosmetics for hair, cosmetics for ultraviolet protection, cleansing detergent such as a hand cleanser, pre-shaving lotion, after shaving lotion, an aromatic agent, dentifrice, ointment, and a patch. Examples of the cosmetics for skin include cosmetic lotion, milky lotion (whitening emulsion, etc.), cream, essence, pack, foundation, sunscreen cosmetic, sun-tanning cosmetic, and various types of lotions. Examples of the cream include cold cream, vanishing cream, massage cream, emollient cream, cleansing cream, moisture cream, and hand cream. Examples of the make-up cosmetic include makeup base, foundation, eye shadow, and cheek shadow. Examples of the cosmetics for hair include shampoo, hair treatment, hair conditioner, two-in-one shampoo, hair-styling cosmetic (hair foam, a hair styling gel, etc.), a hair treatment, hair wax, and a hair dye. Examples of the hair treatment agent include hair cream, treatment lotion, and hair milk lotion. Furthermore, the cosmetic for hair may include a lotion-type hair growth agent or hair tonic, etc. The above-described specific examples of the cosmetic of the present invention are only several examples, and thus, the cosmetic of the present invention is not limited thereto.

Moreover, the cosmetic of the present invention can also comprise additives, depending on the type of the cosmetic of interest, in a range that does not impair the effects of the present invention. Examples of the additives include the following, but are not limited thereto:

hydrocarbon oils such as liquid paraffin or vaseline, vegetable oils and fats, waxes, synthetic ester oil, and silicon-based oil phase components; and higher alcohols, lower alcohols, fatty acids, an ultraviolet absorber, inorganic/organic pigment, color materials, various types of surfactants, polyhydric alcohol, sugars, a high molecular compound, a physiologically active ingredient, a transdermal absorption promoting agent, a solvent, an antioxidant, a pH adjuster, and flavor, etc. Examples of various types of surfactant as described above include a nonionic surfactant, a cationic surfactant, and an amphoteric surfactant.

Furthermore, according to the present invention, there is provided a cellulose-containing composition used to create cosmetic formulas, wherein the cellulose-containing composition comprises the following components (A) and (B):
(A) ultrafine cellulose fibers having a fiber width of 1000 nm or less; and
(B) a water-soluble polymer.

Details of the components (A) and (B) are as described above in the present description.

EXAMPLES

The present invention will be described in the following examples. However, these examples are not intended to limit the scope of the present invention. The mixed amount is indicated with % by mass.

Example 1

<Production of Ultrafine Cellulose Fibers>

(Production Example 1) Production of Ultrafine Cellulose Fibers 1

100 g of urea, 55.3 g of sodium dihydrogen phosphate dihydrate, and 41.3 g of disodium hydrogen phosphate were dissolved in 109 g of water to prepare a phosphorylation reagent.

A formed sheet made of dried needle-leaved tree bleached kraft pulp was treated with a cutter mill and a pin mill to prepare flocculent fibers. 100 g (absolute dry mass) of these flocculent fibers were weighed, and using a spray, the phosphorylation reagent was uniformly sprayed to the fibers. Thereafter, the resulting fibers were kneaded by hands to obtain drug-impregnated pulp.

The obtained drug-impregnated pulp was subjected to a heat treatment for 80 minutes in a damped air drying machine that had been heated to 140° C., so as to obtain phosphorylated pulp.

Thereafter, 100 g (pulp mass) of the obtained phosphorylated pulp was weighed, and 10 L of ion exchange water was then poured therein. The fibers were uniformly dispersed by stirring, and the obtained mixture was then subjected to filtration and dehydration to obtain a dehydration sheet. This step was repeatedly carried out twice. Subsequently, the obtained dehydration sheet was diluted with 10 L of ion exchange water. While stirring, a 1 N sodium hydroxide aqueous solution was gradually added to obtain pulp slurry with a pH value of 12 to 13. Thereafter, this pulp slurry was dehydrated to obtain a dehydration sheet, and 10 L of ion exchange water was then added thereto. The obtained mixture was uniformly dispersed by stirring, and was then subjected to filtration and dehydration to obtain a dehydration sheet. This step was repeatedly carried out twice. The obtained dehydration sheet was measured by the FT-IR measurement of infrared absorption spectra. As a result, absorption based on a phosphoric acid group was observed at 1230 to 1290 cm$^{-1}$, so that addition of the phosphoric acid group could be confirmed. Accordingly, in the obtained dehydration sheet (phosphoric acid-oxo acid introduced cellulose), a portion of the hydroxy groups of the cellulose was substituted by a functional group represented by the following structural formula (1):

[Formula 1]

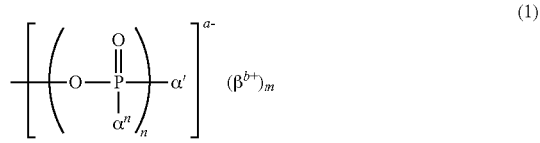

(1)

wherein, a, b, m, and n each independently represent a natural number (provided that a=b×m). In additional, $\alpha^1$, $\alpha^2$, ..., $\alpha^n$ and $\alpha'$ each independently represent R or OR. R represents any one of a hydrogen atom, a saturated straight chain hydrocarbon group, a saturated branched chain hydrocarbon group, a saturated cyclic hydrocarbon group, an un saturated straight chain hydrocarbon group, an un saturated branched chain hydrocarbon group, an aromatic group, and a derivative thereof β represents mono- or more-valent cation consisting of an organic or inorganic matter.

Ion exchange water was added to the obtained phosphorylated cellulose to prepare 2% by mass of slurry. This slurry was subjected to a defibration treatment for 180 minutes using a defibration treatment device (CLEARMIX-11S, manufactured by M Technique Co., Ltd.) under conditions of 6900 rotations/min, so as to obtain a cellulose suspension. As a result of X-ray diffraction, it was found that the cellulose maintained cellulose type I crystals. This cellulose suspension was further passed through a wet-type atomizing device ("ALTIMIZER" manufactured by Sugino Machine Ltd.) at a pressure of 245 MPa once, so as to obtain cellulose fiber 1. As a result of X-ray diffraction, it was found that the cellulose maintained cellulose type I crystals.

(Production Example 2) Production of Ultrafine Cellulose Fibers 2

Cellulose fiber 2 was obtained by the same method as that applied in Production Example 1, with the exception that the cellulose suspension was passed through a wet-type atomizing device ("ALTIMIZER" manufactured by Sugino Machine Ltd.) at a pressure of 245 MPa, 10 times. As a result of X-ray diffraction, it was found that the cellulose maintained cellulose type I crystals.

(Production Example 3) Production of Ultrafine Cellulose Fibers 3

Cellulose fiber 3 was obtained by the same method as that applied in Production Example 1, with the exception that the phosphorylated pulp obtained in Production Example 1 was impregnated with a phosphorylating reagent again, and was then subjected to a heat treatment for 80 minutes in a damped air drying machine that had been heated to 140° C., so that the phosphorylation reaction was carried out twice. As a result of X-ray diffraction, it was found that the cellulose maintained cellulose type I crystals.

(Production Example 4) Production of Ultrafine Cellulose Fibers 4

Cellulose fiber 4 was obtained by the same method as that applied in Production Example 1, with the exception that the phosphorylated pulp obtained in Production Example 1 was impregnated with a phosphorylating reagent again, and was then subjected to a heat treatment for 50 minutes in a damped air drying machine that had been heated to 140° C., so that the phosphorylation reaction was carried out twice. As a result of X-ray diffraction, it was found that the cellulose maintained cellulose type I crystals.

(Production Example 5) Production of Ultrafine Cellulose Fibers 5

Cellulose fiber 5 was obtained by the same method as that applied in Production Example 1, with the exception that the amounts of sodium dihydrogen phosphate dihydrate and disodium hydrogen phosphate were changed to 5.5 g and 4.1 g, respectively. As a result of X-ray diffraction, it was found that the cellulose maintained cellulose type I crystals.

(Measurement of Amount of Phosphoric Acid Group Introduced (Amount of Substituent))

The difference between the amounts of the phosphoric acid group-derived strongly acidic group and weakly acidic group introduced serves as a measure of the condensation of the phosphoric acid group. A smaller value of this difference confers more highly transparent slurry containing the ultrafine cellulose fibers with lower condensation of the phosphoric acid group. The amounts of the phosphoric acid group-derived strongly acidic group and weakly acidic group introduced were measured by directly diluting the ultrafine cellulose fibers-containing slurry after completion of the defibration treatment with ion exchange water to have a solid concentration of 0.2% by mass, followed by a treatment with an ion exchange resin and titration using an alkali.

In the treatment with an ion exchange resin, a strongly acidic ion exchange resin (Amberjet 1024; Organo Corp.; conditioning agent) was added at a volume ratio of 1/10 to the slurry containing 0.2% by mass of ultrafine cellulose fibers, followed by a shake treatment for 1 hour. Then, the suspension was poured to a mesh having an opening of 90 μm, so that the slurry was separated from the resin. In the titration using an alkali, while a 0.1 N sodium hydroxide aqueous solution was added to the ultrafine cellulose fibers-containing slurry after completion of the ion exchange, a change in the values of electrical conductivity exhibited by the slurry was measured.

Specifically, the amount of the alkali (mmol) required for the first region in the curve shown in FIG. 1 was divided by the solid content (g) in the slurry to be titrated to determine the amount of the strongly acidic group introduced (mmol/g). Also, the amount of the alkali (mmol) required for the second region in the curve shown in FIG. 1 was divided by the solid content (g) in the slurry to be titrated to determine the amount of the weakly acidic group introduced (mmol/g).

(Production Example 6) Production of Ultrafine Cellulose Fibers 6

Undried needle-leaved tree bleached kraft pulp equivalent to a dry mass of 200 g, 2.5 g of TEMPO, and 25 g of sodium bromide were dispersed in 1500 ml of water. Thereafter, a 13% by mass of sodium hypochlorite aqueous solution was added to the solution, such that the amount of sodium hypochlorite could be 5.0 mmol with respect to 1.0 g of the pulp, so as to start a reaction. During the reaction, a 0.5 M sodium hydroxide aqueous solution was added dropwise to the reaction solution, so that the pH was kept at 10 to 11. At a time point at which no change was observed in the pH value, the reaction was terminated.

Thereafter, this slurry was dehydrated to obtain a dehydration sheet, and 10 L of ion exchange water was then added thereto. Subsequently, the fibers were uniformly dispersed by stirring, and the obtained mixture was then subjected to filtration and dehydration to obtain a dehydration sheet. This step was repeatedly carried out twice. The obtained dehydration sheet was measured by the FT-IR measurement of infrared absorption spectra. As a result, absorption based on a carboxyl group was observed at 1730 $cm^{-1}$, so that addition of the carboxyl group could be confirmed. Using this dehydration sheet (TEMPO oxidized cellulose), ultrafine cellulose fibers was prepared.

Ion exchange water was added to the thus obtained carboxyl group-added TEMPO oxidized cellulose to prepare 2% by mass of shiny. This slurry was subjected to a defibration treatment for 180 minutes using a defibration treatment device (CLEARMIX-11S, manufactured by M Technique Co., Ltd.) under conditions of 6900 rotations/min, so as to obtain a cellulose suspension. As a result of X-ray diffraction, it was found that the cellulose maintained cellulose type I crystals. This cellulose suspension was further passed through a wet-type atomizing device ("ALTIMIZER" manufactured by Sugino Machine Ltd.) at a pressure of 245 MPa, 10 times, so as to obtain cellulose fiber 6.

As a result of X-ray diffraction, it was found that the cellulose maintained cellulose type I crystals.

[Example 2] Measurement of Viscosity and Crystallinity

Cellulose fibers 1 to 6 were measured in terms of viscosity according to the following method.

Water was added to each of the cellulose fibers 1 to 6, and the concentration of each cellulose fiber was adjusted to 0.4% by mass. Suspensions of the cellulose fiber 1 to 6 were left for 24 hours, and thereafter, the viscosity of each cellulose fiber was measured at 25° C. at a rotation number of 3 rpm (3 min), using a B-type viscometer (analog viscometer T-LVT, manufactured by BLOOKFIELD). The results are shown in Table 1.

Cellulose fibers 1 to 6 were measured in terms of fiber width according to the following method.

A supernatant of defibrated pulp slurry was diluted with water to a concentration of 0.01% to 0.1% by mass, and the obtained solution was then added dropwise onto a hydrophilized carbon grid film After drying, it was stained with uranyl acetate, and was then observed under a transmission electron microscope (JEOL-2000EX, manufactured by JEOL). In Production Examples 1 to 4 and Production Example 6, it was confirmed that ultrafine cellulose fibers having a width of approximately 4 nm were obtained. In Production Example 5, ultrafine cellulose fibers having a fiber width of approximately 4 nm could not be observed. The defibrated pulp slurry of Production Example 5 was diluted with water to a concentration of 0.01% to 0.1% by mass, and was then added dropwise onto a slide glass. A cover glass was covered on it, and it was then observed under a digital microscope (KH-7700, manufactured by Hirox). As a result, coarse fibers with a size of 10 μm or more were observed.

Regarding the crystallinity of cellulose fibers 1 to 6, it was measured using an X-ray diffractometer, and was then obtained according to the following calculation formula. It is to be noted that the "crystallization index" in the following calculation formula is also referred to as "crystallinity."

$$\text{Cellulose type } I \text{ crystallization index } (\%) = [(I_{22.6} - I_{18.5})/I_{22.6}] \times 100 \quad (1)$$

[wherein $I_{22.6}$ represents the diffraction intensity of a lattice plane (002 plane) in X-ray diffraction (diffraction angle 2θ=22.6°), and $I_{18.5}$ represents the diffraction intensity of an amorphous portion (diffraction angle 2θ=18.5°)].

$$0.45 \leq \alpha \omega (m \cdot \text{rad/sec}) \quad (2)$$

[wherein α represents a half amplitude (m), and ω represents an angular velocity (rad/sec)].

TABLE 1

| | | Concentration (%) | Type of substituent | Amount of substituent (mmol/g) | Viscosity (mPa · S) | Crystallinity (%) |
|---|---|---|---|---|---|---|
| Production Example 1 | Cellulose fiber 1 | 0.4 | Phosphoric acid group | 0.71 | 14820 | 85 |
| Production Example 2 | Cellulose fiber 2 | 0.4 | Phosphoric acid group | 0.71 | 2970 | 85 |
| Production Example 3 | Cellulose fiber 3 | 0.4 | Phosphoric acid group | 1.7 | 15600 | 80 |
| Production Example 4 | Cellulose fiber 4 | 0.4 | Phosphoric acid group | 0.15 | 3765 | 80 |
| Production Example 5 | Cellulose fiber 5 | 0.4 | Phosphoric acid group | 0.09 | 770 | 88 |
| Production Example 6 | Cellulose fiber 6 | 0.4 | Carboxyl group | 1.2 | 2540 | 84 |

As shown in Table 1, the suspensions of cellulose fibers 1 to 4 and 6 had sufficient viscosity. Regarding cellulose fiber 5, the phosphorylation reaction was not sufficient, and after completion of defibration, only coarse fibers having a fiber width of 10 μm or more were observed, and fine monofibers having a fiber width of 1000 nm or less were not found. Thus, the cellulose fiber 5 did not exhibit sufficient viscosity.

Example 3

<Evaluation of Cosmetics>

Individual cosmetics shown in the following Tables 2 and 3 were prepared, and were then analyzed in terms of formulation stability, and the sensory texture (the presence or absence of stickiness) was evaluated. The results are also shown in Tables 2 and 3. The term "To 100" used in Tables 2 and 3 indicates a balance amount that sets the total amount to 100. Moreover, the inventions and comparative products shown in Tables 2 and 3 each comprise, as pH adjusters, citric acid (0.05% by mass based on the mass of the entire cosmetic) and sodium citrate (0.01% by mass based on the mass of the entire cosmetic). Besides, evaluation was carried out according to the following criteria.

(1) Method for Preparing Cosmetics

Individual components in a water phase were heated and dissolved, and were then uniformly dispersed in advance. Thereafter, the dispersion was mixed with an oil phase adjusted to 80° C., and the mixture was then emulsified using a homogenizer (5000 rpm, 5 minutes).

(2) Evaluation of Formulation Stability

The prepared cosmetics were each left at 45° C. for 1 month, and the formulation stability thereof was then evaluated. Evaluation criteria are as follows.

A: Glossy appearance, in which separation of oil or water is not observed at all B: Glossy but rough appearance, in which separation of oil or water is not observed C: Matt appearance, in which separation of oil or water is not observed D: Separation of oil or water is clearly observed, or is insufficiently dispersed (3) Evaluation of Stickiness after Use An actual use test was carried out with 10 professional panelists. Evaluation criteria are as follows.

A: 8 or more panelists recognize that there is no stickiness after use.

B: 6 or more and less than 8 panelists recognize that there is no stickiness after use.

C: 3 or more and less than 6 panelists recognize that there is no stickiness after use.

D: Less than 3 panelists recognize that there is no stickiness after use.

TABLE 2

| | | Invention 1 | Invention 2 | Invention 3 | Invention 4 | Invention 5 | Invention 6 | Comp. Product 1 | Comp. Product 2 | Comp. Product 3 | Comp. Product 4 |
|---|---|---|---|---|---|---|---|---|---|---|---|
| Water phase | Cellulose fiber 1 | 0.5 | | | | 0.5 | | 0.5 | | | |
| | Cellulose fiber 2 | | 0.5 | | | | | | | | |
| | Cellulose fiber 3 | | | 0.5 | | | | | | 0.5 | |
| | Cellulose fiber 4 | | | | 0.5 | | | | | | |
| | Cellulose fiber 5 | | | | | | | | | | 0.5 |
| | Cellulose fiber 6 | | | | | | 0.5 | | | | |
| | Xanthan gum | 0.1 | 0.1 | 0.1 | 0.1 | | 0.1 | | | 0.1 | 0.6 |
| | Carboxymethyl cellulose | | | | | 0.1 | | | | | |
| | Butylene glycol | 7.0 | 7.0 | 7.0 | 7.0 | 7.0 | 7.0 | 7.0 | 7.0 | 7.0 | 7.0 |
| | Stearoylmethyl-taurine sodium | 0.5 | 0.5 | 0.5 | 0.5 | 0.5 | 0.5 | 0.5 | 0.5 | 0.5 | 0.5 |
| | Water | To 100 | To 100 | To 100 | To 100 | To 100 | To 100 | To 100 | To 100 | To 100 | To 100 |
| | Preservative | Proper quantity | Proper quantity | Proper quantity | Proper quantity | Proper quantity | Proper quantity | Proper quantity | Proper quantity | Proper quantity | Proper quantity |
| | pH adjuster | Proper quantity | Proper quantity | Proper quantity | Proper quantity | Proper quantity | Proper quantity | Proper quantity | Proper quantity | Proper quantity | Proper quantity |
| Oil phase | Sorbitan fatty acid ester | 2.5 | 2.5 | 2.5 | 2.5 | 2.5 | 2.5 | 2.5 | 2.5 | 2.5 | 2.5 |
| | Polyoxyethylene hydrogenated castor oil | 1.2 | 1.2 | 1.2 | 1.2 | 1.2 | 1.2 | 1.2 | 1.2 | 1.2 | 1.2 |
| | Ethylhexyl palmitate | 19.0 | 19.0 | 19.0 | 19.0 | 19.0 | 19.0 | 19.0 | 19.0 | 19.0 | 19.0 |
| | Fine particle zinc oxide | 15.0 | 15.0 | 15.0 | 15.0 | 15.0 | 15.0 | 15.0 | 15.0 | 15.0 | 15.0 |
| Evaluation | Formulation stability | A | A | A | A | A | C | D | D | D | C |
| | Formulation stickiness | A | A | A | A | A | C | C | C | D | D |

As shown in Table 2, the formulations of Inventions 1 to 5 comprising ultrafine cellulose fibers having an ionic substituent and a water-soluble polymer were glossy formulations having uniformity. The formulations did not have stickiness and were excellent in terms of sense of use. The formulation of Invention 6 was inferior to Inventions 1 to 5, but it also provided results showing a good balance between formulation stability and suppression of the stickiness thereof.

In contrast, the formulations of Comparative Products 1 and 2, which did not comprise a water-soluble polymer, were gloss-free, Aggregates, which seemed to be derived from ultrafine cellulose fibers, could be confirmed even by visual observation, and thus, the formulations provided rough feeling.

Since the formulation of Comparative Product 4 did not comprise ultrafine cellulose fibers, it had stickiness. Regarding Comparative Product 3, good results could not be obtained in the evaluation of both formulation stability and formulation stickiness.

TABLE 3

| | | Invention 7 | Invention 8 | Invention 9 | Invention 10 | Invention 11 | Invention 12 | Invention 13 | Invention 14 |
|---|---|---|---|---|---|---|---|---|---|
| Water phase | Cellulose fiber 3 | 0.3 | 0.4 | 0.2 | 0.5 | 0.5 | 0.5 | 0.3 | 0.5 |
| | Xanthan gum | 0.1 | 0.1 | 0.4 | 0.05 | | | | |
| | Carrageenan | | | | | | | 0.1 | 0.1 |
| | Hydroxyethyl cellulose | | | | | 0.1 | 0.3 | | |
| | Butylene glycol | 7.0 | 7.0 | 7.0 | 7.0 | 7.0 | 7.0 | 7.0 | 7.0 |
| | Stearoylmethyl-taurine sodium | 0.5 | 0.5 | 0.5 | 0.5 | 0.5 | 0.5 | 0.5 | 0.5 |
| | Water | To 100 | To 100 | To 100 | To 100 | To 100 | To 100 | To 100 | To 100 |
| | Preservative | Proper quantity | Proper quantity | Proper quantity | Proper quantity | Proper quantity | Proper quantity | Proper quantity | Proper quantity |
| | pH adjuster | Proper quantity | Proper quantity | Proper quantity | Proper quantity | Proper quantity | Proper quantity | Proper quantity | Proper quantity |
| Oil phase | Sorbitan fatty acid ester | 2.5 | 2.5 | 2.5 | 2.5 | 2.5 | 2.5 | 2.5 | 2.5 |
| | Polyoxyethylene hydrogenated castor oil | 1.2 | 1.2 | 1.2 | 1.2 | 1.2 | 1.2 | 1.2 | 1.2 |
| | Ethylhexyl palmitate | 19.0 | 19.0 | 19.0 | 19.0 | 19.0 | 19.0 | 19.0 | 19.0 |
| | Fine particle zinc oxide | 15.0 | 15.0 | 15.0 | 15.0 | 15.0 | 15.0 | 15.0 | 15.0 |
| Evaluation | Formulation stability | A | A | B | B | A | B | A | A |
| | Formulation stickiness | A | A | B | A | A | B | A | A |

As shown in Table 3, the formulations of Inventions 7 to 14, in which ultrafine cellulose fibers were mixed with a water-soluble polymer at a ratio shown in each of Inventions 7 to 14, were glossy formulations having uniformity. The formulations did not have stickiness and were excellent in terms of sense of use.

Hereafter; application examples of the present invention, in which (A) ultrafine cellulose fibers were mixed with (B) a water-soluble polymer, are given. However, these application examples are not intended to limit the present invention. Moreover, in Examples 4 to 10, it was confirmed by the method of Example 3 that the cosmetic products had excellent formulation stability and no sticky feeling.

[Example 4] Viscous Lotion

| (A) | Cellulose fiber 4 | 0.50 (% by mass) |
|---|---|---|
|  | Hydroxyethyl cellulose | 0.05 |
|  | Glycerin | 7.00 |
|  | 1,3-Butylene glycol | 5.00 |
|  | Preservative | Proper quantity |
|  | Purified water | Balance |
| (B) | Dipotassium glycyrrhizinate | 0.10 |
|  | Purified water | 10.00 |

Preparation method: A is heated to 80° C., and is then cooled to 40° C. while stirring. While A is stirred, B is added thereto. The mixture is further cooled while stirring, and the preparation is then terminated at room temperature.

[Example 5] Gel Essence

| (A) | Cellulose fiber 3 | 0.30 (% by mass) |
|---|---|---|
|  | Xanthan gum | 0.05 |
|  | Glycerin | 3.00 |
|  | 1,3-Butylene glycol | 7.00 |
|  | Preservative | Proper quantity |
|  | Purified water | Balance |
| (B) | Arginine | 0.05 |
|  | Purified water | 5.00 |
| (C) | Dipotassium glycyrrhizinate | 0.10 |
|  | Sodium hyaluronate (1% aqueous solution) | 3.00 |
|  | Purified water | 5.00 |

Preparation method: A is heated to 80° C., and is then cooled to 40° C. while stirring. While A is stirred, B and C are each added thereto. The mixture is further cooled while stirring, and the preparation is then terminated at room temperature.

[Example 6] Gel Milky Lotion

| (A) | Cellulose fiber 2 | 1.00 (% by mass) |
|---|---|---|
|  | Guar gum | 0.10 |
|  | Glycerin | 8.00 |
|  | 1,3-Butylene glycol | 5.00 |
|  | Arginine | 0.70 |
|  | Perservative | Proper quantity |
|  | Purified water | Balance |
| (B) | Jojoba oil | 3.00 |
|  | Squalane | 5.00 |
|  | Cetyl phosphate | 1.40 |
|  | Stearyl alcohol | 2.00 |

Preparation method: A and B are each heated to 80° C. for uniform dissolution. A is added to B, and the mixture is then emulsified by stirring it. The mixture is cooled to room temperature while stirring, and preparation is terminated.

[Example 7] Foundation

| (A) | Cellulose fiber 3 | 0.70 (% by mass) |
|---|---|---|
|  | Carboxymethyl cellulose | 0.10 |
|  | Stearoylmethyltaurine sodium | 0.50 |
|  | 1,3-Butylene glycol | 5.00 |
|  | Preservative | Proper quantity |
|  | Purified water | Balance |
| (B) | Pigment titanium oxide | 7.00 |
|  | Iron oxide (yellow) | 0.70 |
|  | Iron oxide (red) | 0.20 |
|  | Iron oxide (black) | 0.10 |
| (C) | NIKKOL, NIKKOMULESE 41 | 2.50 |
|  | Glyceryl stearate | 1.00 |
|  | Cetostearyl alcohol | 1.00 |
|  | Ethylhexyl methoxycinnamate | 8.00 |
|  | Dimethicone (6cs) | 3.00 |
|  | Cyclopentasiloxane | 5.00 |

* NIKKOL, NIKKOMULESE 41: behenyl alcohol, polyglyceryl-10 pentastearate, and sodium stearoyl lactylate Preparation method: B is previously blended using a mill, so that it is uniformly dispersed. A and C are each heated to 80° C. for uniform dissolution. Thereafter, B is added to A, and C is then added to the mixture, while A is homogenized, so that they are emulsified. The obtained mixture is cooled to room temperature while stirring, and preparation is terminated.

[Example 8] Sunscreen Lotion

| (A) | Cellulose fiber 4 | 0.05 (% by mass) |
|---|---|---|
|  | Guar gum | 0.03 |
|  | Glycerin | 5.00 |
|  | Preservative | Proper quantity |
|  | Purified water | Balance |
| (B) | CM3K40T4J | 35.00 |
|  | CM3K50XZ4J | 25.00 |
|  | X-21-5250L | 3.00 |
|  | Cyclopentasiloxane | 15.00 |
|  | (Vinyldimethicone/ methiconesilsesquioxane) cross polymer | 2.00 |

* CM3K40T4J: PEG-10 dimethicone, fine particle titanium oxide, cyclopentasiloxane, methicone, and alumina
CM3K50XZ4J: PEG-10 dimethicone, methicone, fine particle zinc oxide, and cyclopentasiloxane
X-21-5250L: trimethyl siloxysilicate, and dimethicone Preparation method: B is stirred at room temperature, so that it is uniformly dispersed. A is added to B, while stirring. The obtained mixture is then stirred, and preparation is terminated.

[Example 9] Sunscreen Gel

| (A) | Cellulose fiber 3 | $1.00 (% by mass) |
|---|---|---|
|  | Xanthan gum | 0.50 |
|  | Nylon-12 | 2.00 |
|  | 1,3-Butylene glycol | 5.00 |
|  | Preservative | Proper quantity |
|  | Purified water | Balance |

|     |                |       |
| --- | -------------- | ----- |
| (B) | PEG-10 dimethicone | 0.50 |
|     | CM3K40T4J      | 25.00 |
|     | CM3K50XZ4J     | 15.00 |

\* CM3K40T4J: PEG-10 dimethicone, fine particle titanium oxide, cyclopentasiloxane, methicone, and alumina
CM3K50XZ4J: PEG-10 dimethicone, methicone, fine particle zinc oxide, and cyclopentasiloxane Preparation method: A is heated to 80° C., so that it is uniformly dissolved. Then, A is cooled to room temperature, while stirring. B is added to A, while A is stirred with a homogenizer, the mixture is emulsified, and the preparation is then terminated.

[Example 10] Sunscreen Milk

|     |                                    |                 |
| --- | ---------------------------------- | --------------- |
| (A) | Cellulose fiber 3                  | 0.30 (% by mass) |
|     | Xanthan gum                        | 0.05            |
|     | Stearoylmethyltaurine sodium       | 0.50            |
|     | 1,3-Butylene glycol                | 5.00            |
|     | Preservative                       | Proper quantity |
|     | Purified water                     | Balance         |
| (B) | PEG-60 hydrogenated castor oil     | 0.50            |
|     | Polysorbate 60                     | 0.70            |
|     | Sorbitan stearate                  | 1.50            |
|     | IOP50XZ4J                          | 25.00           |
|     | IOPP40VMJ                          | 25.00           |
|     | Ethylhexyl methoxycinnamate        | 8.00            |
|     | Diethylamino hydroxybenzoyl hexyl benzoate | 3.00    |

\* IOP50XZ4J: ethylhexyl palmitate, fine particle zinc oxide, methicone, and polyhydroxystearic acid
IOPP40VMJ: ethylhexyl palmitate, fine particle titanium oxide, alumina, methicone, and polyhydroxystearic acid Preparation method: A and B are each heated to 80° C., so that they are uniformly dissolved. B is added to A, while A is stirred with a homogenizer, and the mixture is emulsified. The mixture is cooled to room temperature while stirring, and the preparation is then terminated.

[Example 11] Hair Mist

|     |                                          |                 |
| --- | ---------------------------------------- | --------------- |
| (A) | Cellulose fiber 1                        | 0.70 (% by mass) |
|     | Hydroxypropylmethylcellulose stearoxy ether | 0.20         |
|     | Preservative                             | Proper quantity |
|     | Purified water                           | Balance         |
| (B) | Ethylhexyl methoxycinnamate              | 0.50            |
|     | 1,3-Butylene glycol                      | 3.00            |
|     | PPG-6-DECYLTETRADECETH-30                | 1.00            |
| (C) | Pantenol                                 | 0.70            |
|     | Ethanol                                  | 10.00           |

Preparation method: A is heated to 80° C., so that it is uniformly dissolved. Then, A is cooled to room temperature, while stirring. B and C are each added to A, while A is stirred, so that they are uniformly dispersed. Thereafter, preparation is terminated.

[Example 12] Hair Cream

|     |                   |                 |
| --- | ----------------- | --------------- |
| (A) | Cellulose fiber 2 | 0.50 (% by mass) |
|     | Xanthan gum       | 0.10            |
|     | Arginine          | 0.70            |
|     | Preservative      | Proper quantity |
|     | Purified water    | Balance         |
| (B) | Hydrogenated lecithin          | 1.00 |
|     | Polyglyceryl-10 myristate      | 1.00 |
|     | Cetyl alcohol                  | 1.50 |
|     | Triethylhexanoin               | 8.00 |
|     | Cyclopentasiloxane             | 5.00 |
|     | Highly polymerized dimethicone | 3.00 |
|     | Ethylhexyl methoxycinnamate    | 1.50 |

Preparation method: A and B are each heated to 80° C., so that they are uniformly dissolved. B is added to A, while A is stirred, and the mixture is emulsified. The mixture is cooled to room temperature while stirring, and the preparation is then terminated.

INDUSTRIAL APPLICABILITY

The present invention can provide a cosmetic having a good sensory texture upon application and high formulation stability.

The invention claimed is:

1. A cosmetic comprising the following components (A) and (B):
   (A) ultrafine cellulose fibers having a fiber width of 1000 nm or less; and
   (B) a water-soluble polymer,
   wherein the ultrafine cellulose fibers have an ionic substituent,
   wherein an amount of the ionic substituent introduced is 0.1 mmol/g to 3.0 mmol/g based on 1 g of ultrafine cellulose fibers,
   wherein the ionic substituent is a phosphoric acid-derived substituent, and
   wherein the water-soluble polymer is xanthan gum, carrageenan, cationized starch, or cationized guar gum.

2. The cosmetic according to claim 1, wherein the component (A) is mixed in an amount of 0.01% to 2.0% by mass based on the mass of the entire cosmetic.

3. The cosmetic according to claim 1, wherein the component (B) is mixed in an amount of 0.03% to 1.0% by mass based on the mass of the entire cosmetic.

4. The cosmetic according to claim 1, which further comprises, as a component (C), one or two or more selected from the group consisting of inorganic powder, organic powder, inorganic acid, organic acid, inorganic acid salt, organic acid salt, and an anionic surfactant.

5. A cellulose-containing composition for use in forming a cosmetic, wherein the cellulose-containing composition comprises the following components (A) and (B):
   (A) ultrafine cellulose fibers having a fiber width of 1000 nm or less; and
   (B) a water-soluble polymer,
   wherein the ultrafine cellulose fibers have an ionic substituent,
   wherein an amount of the ionic substituent introduced is 0.1 mmol/g to 3.0 mmol/g based on 1 g of ultrafine cellulose fibers,
   wherein the ionic substituent is a phosphoric acid-derived substituent, and
   wherein the water-soluble polymer is xanthan gum, carrageenan, cationized starch, or cationized guar gum.

6. A cosmetic method which comprises applying, to living body, a cosmetic comprising the following components (A) and (B):
   (A) ultrafine cellulose fibers having a fiber width of 1000 nm or less; and (B) a water-soluble polymer,
wherein the ultrafine cellulose fibers have an ionic substituent,
wherein an amount of the ionic substituent introduced is 0.1 mmol/g to 3.0 mmol/g based on 1 g of ultrafine cellulose fibers, wherein the ionic substituent is a phosphoric acid-derived substituent, and
wherein the water-soluble polymer is xanthan gum, carrageenan, cationized starch, or cationized guar gum.

7. The cosmetic method according to claim 6, wherein the component (A) is mixed in an amount of 0.01% to 2.0% by mass based on the mass of the entire cosmetic.

8. The cosmetic method according to claim 6, wherein the component (B) is mixed in an amount of 0.03% to 1.0% by mass based on the mass of the entire cosmetic.

9. The cosmetic method according to claim 6, wherein the cosmetic further comprises, as a component (C), one or two or more selected from the group consisting of inorganic powder, organic powder, inorganic acid, organic acid, inorganic acid salt, organic acid salt, and an anionic surfactant.

10. The cosmetic according to claim 1, wherein the ionic substituent is introduced by chemical treatment.

11. The cellulose-containing composition according to claim 5, wherein the ionic substituent is introduced by chemical treatment.

12. The cosmetic method according to claim 6, wherein the ionic substituent is introduced by chemical treatment.

* * * * *